US00PP26775P3

(12) United States Plant Patent
Helvick et al.

(10) Patent No.: US PP26,775 P3
(45) Date of Patent: May 31, 2016

(54) ***VITEX* PLANT NAMED 'PIIVAC-II'**

(50) Latin Name: ***Vitex agnus-castus* L.**
Varietal Denomination: PIIVAC-II

(71) Applicant: Plant Introductions, Inc., Watkinsville, GA (US)

(72) Inventors: Rhonda Helvick, Madison, GA (US); Oren McBee, Bishop, GA (US); Mark Griffith, Watkinsville, GA (US); Jeff Beasley, Lavonia, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 110 days.

(21) Appl. No.: 14/121,506

(22) Filed: Sep. 12, 2014

(65) Prior Publication Data

US 2016/0081244 P1 Mar. 17, 2016

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Annette Para
(74) *Attorney, Agent, or Firm* — Lathrop & Gage LLP

(57) ABSTRACT

A new and distinct cultivar of *Vitex* plant named 'PIIVAC-II', characterized by its compact, rounded growth habit, dark green foliage, dark bluish purple flowers, short internodes, and flowers on every terminal.

3 Drawing Sheets

Genus and species of plant claimed: *Vitex agnus-castus* L.
Variety denomination: 'PIIVAC-II'.

BACKGROUND OF THE INVENTION

The present invention relates to a new and distinct cultivar of *Vitex* plant, botanically known as *Vitex agnus-castus* L., commonly known as chastetree, and hereinafter referred to by the cultivar name 'PIIVAC-II'. 'PIIVAC-II' is grown primarily as an ornamental for landscape use and for use as a potted plant.

'PIIVAC-II' originated from an open-pollinated seed of *Vitex agnus-castus*. L. 'PIIVAC-I' (PPAF) growing in Watkinsville, Ga. in 2011. The cultivar 'PIIVAC-II' originated and was selected in a cultivated environment in Watkinsville, Ga. from the progeny of this open-pollination by continued evaluation for growth habit, foliage and flower characteristics.

Asexual reproduction of 'PIIVAC-II' by stem cuttings in Watkinsville, Ga. since 2011 has shown that all the unique features of this new *Vitex*, as herein described, are stable and reproduced true-to-type through successive generations of such asexual propagation.

SUMMARY OF THE INVENTION

Plants of the new cultivar 'PIIVAC-II' have not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIVAC-II' from all other varieties in commerce known to the inventor. 1. Compact, rounded growth habit; 2. Dark green foliage; 3. Dark bluish purple flowers; 4. short internodes; 5. flowers on every terminal.

'PIIVAC-II' is distinguished from its female parent by its growth habit, smaller foliage, short internodes, flower size, and has no central leader. 'PIIVAC-II' has an overall smaller, compact, rounded growth habit, the internodes are shorter, the flowers are smaller in compact racemose-panicles, and forms a multi-branched shrub whereas its female parent has an overall larger, rounded to upright-spreading open-branched growth habit, has longer internode spacing, and larger flowers.

'PIIVAC-II' can be compared to 'Shoal Creek' (unpatented), but differs in the following characteristics. 'PIIVAC-II' has an overall smaller and more compact growth habit than 'Shoal Creek'. 'PIIVAC-II' has smaller foliage than 'Shoal Creek'. 'PIIVAC-II' has smaller inflorescences, but inflorescences on every terminal. 'PIIVAC-II' also has much smaller internode spacing than 'Shoal Creek'. The flower on 'PIIVAC-II' is a darker blue-purple than 'Shoal Creek'.

BRIEF DESCRIPTION OF THE DRAWINGS

The accompanying color photographs illustrate the flower and foliage characteristics and the overall appearance of 'PIIVAC-II', showing the colors as true as it is reasonably possible to obtain in color reproductions of this type. Colors in the photographs may differ slightly from the color values cited in the detailed botanical description which accurately describe the colors of the new *Vitex*.

DETAILED DESCRIPTION

Figure 1:
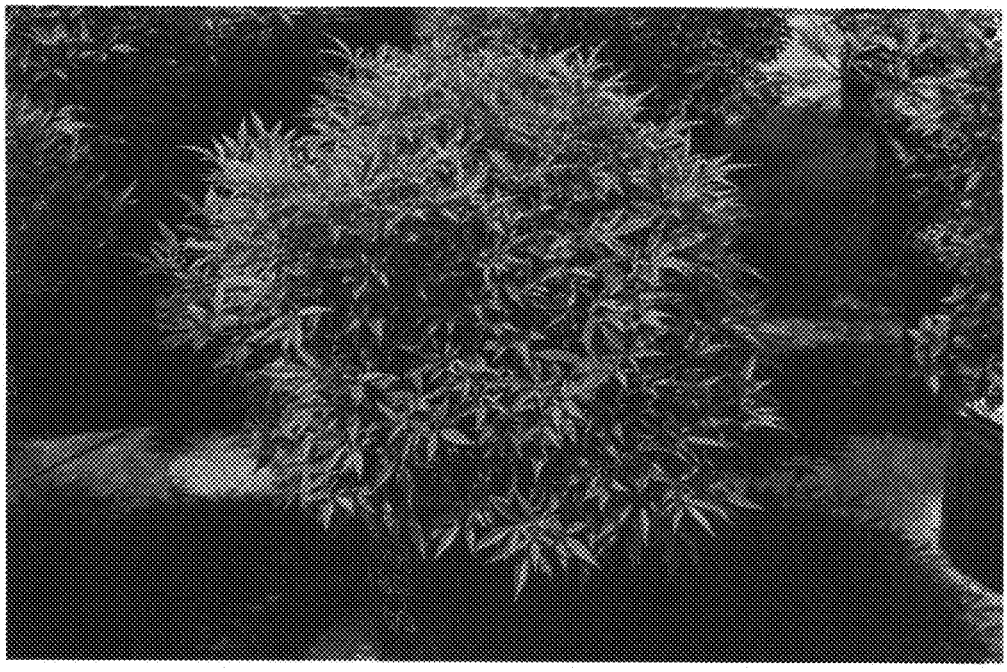
FIG. 1 Illustrates a habit shot of a three-year-old 'PIIVAC-II' plant.
Figure 2:
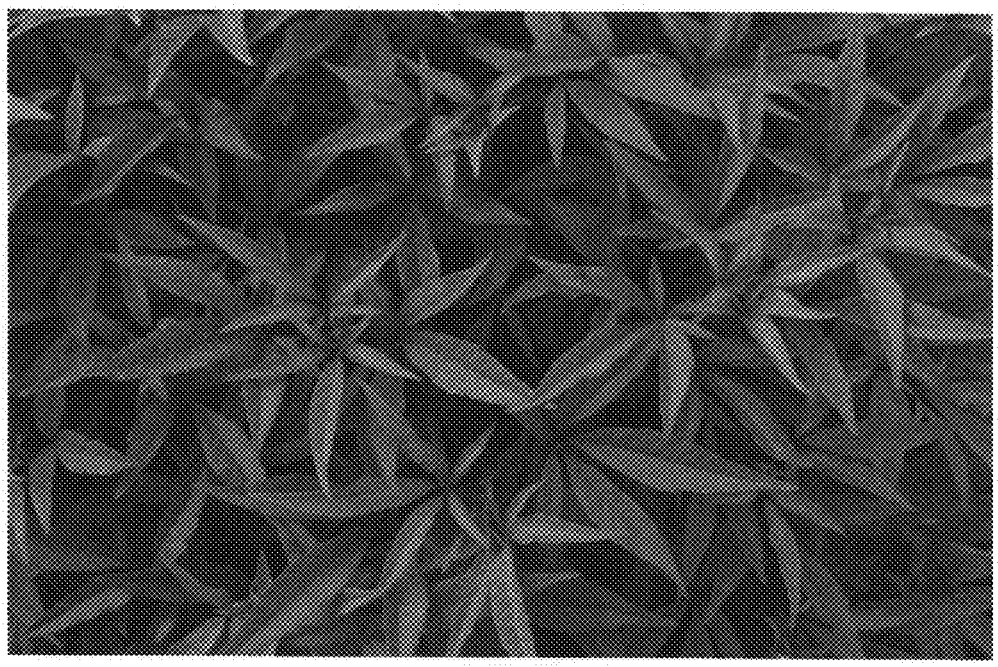
FIG. 2 Illustrates a close-up view of the foliage of a three-year-old 'PIIVAC-II' plant.
Figure 3:
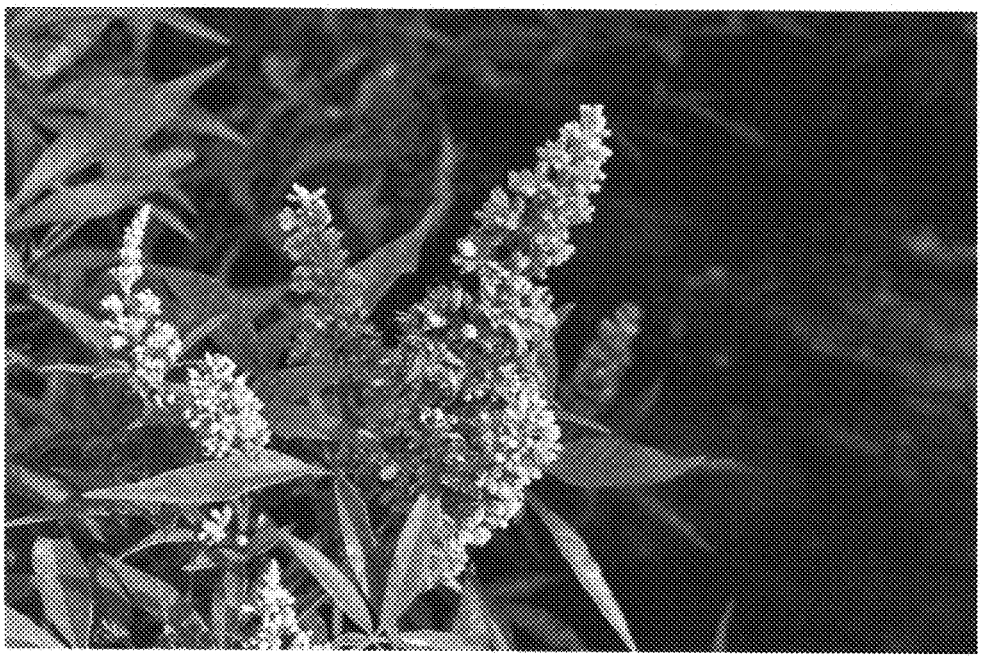
FIG. 3 Illustrates a close-up view of the inflorescences of a three-year-old 'PIIVAC-II' plant.

In the following description, color references are made to The Royal Horticultural Society Colour Chart, 2007 Edition, except where general terms of ordinary dictionary significance are used. The plant used for the description was approximately three years old and was grown in the ground in a 56.78 L container in Watkinsville, Ga.

Botanical classification: *Vitex agnus-castus* L., cultivar 'PIIVAC-II'.

Parentage:

*Female, or seed, parent.*—*Vitex agnus-castus* L. cultivar 'PIIVAC-I' (PPAF).

*Male, or pollen parent.*—Unknown (open-pollinated).

Propagation: Terminal cuttings.

Time to initiate roots, summer: About 28 days at 32° C.

Plant description: Deciduous flowering shrub; compact, rounded growth habit.

*Freely branching.*—Pruning enhances lateral branch development.

*Root description.*—Numerous, fibrous and well-branched.

*Plant size.*—About 59 cm high from the media level to the top of the inflorescences and about 80 cm wide.

*First year stems.*—Have a diameter of about 2 mm. Shape: quadrangular when young, becoming rounded with age. Pubescence: tomentulose.

*Second year and older stems.*—Have a diameter of about 4 mm or more. Shape: round. Texture: glabrous.

*Trunk diameter.*—2 cm at the soil line.

*Color.*—N199A.

*Internode length.*—About 3 cm.

*Strength.*—Flexible when young, becoming stronger with age.

*First year stem color* (*young*).—177C on the upper and lower surface. Color (mature): upper and lower surfaces are 199B.

*Second year and older stem color.*—199B. Bark does not exfoliate.

Vegetative buds: Opposite arrangement, sessile, subglobose, 2 bud scales with tomentulose pubescence.

*Color.*—145B.

*Size.*—About 1.5 mm in length and 1 mm in width.

Foliage description:

*Arrangement.*—Opposite, compound palmate, 5 to 7 leaflets.

*Leaflet length.*—About 7 cm.

*Leaflet width.*—About 1.2 cm.

*Shape.*—Elliptic-ovate to lanceolate.

*Apex.*—Acuminate.

*Base.*—Cuneate.

*Margin.*—Usually entire, occasionally few serrations. Foliage gives off a somewhat spicy odor when crushed.

*Texture.*—Upper surface is glabrous and matte, lower surface is tomentulose.

*Venation pattern.*—Pinnate.

*Venation color* (*upper surface*).—145B.

*Venation color* (*lower surface*).—145B.

*Foliage color* (*upper surface*).—146A.

*Foliage color* (*lower surface*).—143B.

*Petiole length.*—About 3 cm.

*Petiole diameter.*—About 2 mm.

*Petiole color.*—Upper surface is 152D and lower surface is 144B.

*Pubescence.*—Tomentulose.

Flower description: Flowers on new growth. Flowers are produced from about June through September in Watkinsville, Ga. An inflorescence is showy for about two weeks, and individual flowers last about two days and are self-cleaning.

*Fragrance.*—Fragrant.

*Inflorescence type.*—Terminal racemose-panicles.

*Inflorescence length.*—About 8 cm.

*Inflorescence width.*—About 6 cm. An inflorescence contains approximately 250 individual flowers.

*Peduncle.*—About 7 cm in length, about 2 mm in diameter, color is N199B, with tomentulose pubescence.

*Individual flowers.*—About 8 mm in height and 10 mm in diameter.

*Flower buds.*—Length: about 6 mm; Diameter: about 2 mm; Color: 91C.

*Pedicels.*—About 3 mm in length, less than 1 mm in diameter, 145C in color with tomentulose pubescence.

*Calyx.*—Consists of 5 fused sepals with acute apices and 145A in color. The calyx is about 4 mm in length, about 2 mm in diameter, 145A in color with tomentulose pubescence.

*Sepals.*—Arrangement/quantity: single whorl of five fused sepals. Length about 4 mm. Width: about 2 mm. Shape: elliptical. Apex: acute. Margin: entire. Texture upper and lower surface: tomentulose. Color on upper and lower surface: 134B.

Petals:

*Arrangement/appearance.*—5 petals fused at the base to form the corolla tube, which is about 5 mm in length, 3 mm in width and 90B in color. The lower petal is cupped and larger than the other 4 petals which are reflexed.

*Lower petal.*—Length: about 5 mm. Width: about 3 mm. Shape: elongated. Apex: broad obtuse to rounded. Texture: glabrous.

*Upper and lateral petals.*—Length: about 3 mm. Width: about 2.5 mm. Shape: oblong. Apex: broad obtuse to rounded. Texture: glabrous.

*Petal color* (*all petals*).—Upper surface is 90B in color and lower surface is 191D in color.

Stamens:

*Quantity/arrangement.*—4 stamens per flower attached to the inner base of the corolla tube, about 5 mm long, filament color is 91C, and anther color is N92B. The stamens are glabrous.

*Pollen.*—Produced in moderate quantities and is 155B in color.

Pistils:

*Quantity.*—One inferior pistil per flower.

*Pubescence.*—None.

*Pistil.*—About 1 cm in length and about 1.5 mm in width.

*Stigma shape.*—Forked, about 1 mm in width.

*Stigma color.*—155D.

*Style color.*—77C and about 4 mm in length.

*Ovary color.*—143C and about 1 mm in diameter.

Fruit:

*Type/appearance.*—Drupe, rounded to oblong in shape.

*Length.*—About 4 mm.

*Diameter.*—About 3 mm.

*Immature color.*—145B at the base and 178B at the apex.

*Mature color.*—*N*200B. Each drupe contains one seed that is about 3.5 mm long, 2.5 mm wide, and N199A in color.

Plant hardiness:

*Plant hardiness*.—USDA Hardiness Zone Map (2012): Zones 7 to 9.

Disease/pest resistance: Plants of the claimed *Vitex* have not been shown to be resistant to pathogens or pests common to *Vitex*.

I claim:

1. A new and distinct *Vitex* plant named 'PIIVAC-II', as illustrated and described herein.

* * * * *